US009545217B2

United States Patent
Duyn et al.

(10) Patent No.: US 9,545,217 B2
(45) Date of Patent: Jan. 17, 2017

(54) MOVEMENT CORRECTION IN MRI USING A CAMERA

(75) Inventors: Jeff Duyn, Garrett Park, MD (US); Lei Qin, Natick, MA (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 895 days.

(21) Appl. No.: 12/937,852

(22) PCT Filed: Apr. 17, 2009

(86) PCT No.: PCT/US2009/040948
§ 371 (c)(1),
(2), (4) Date: Apr. 11, 2011

(87) PCT Pub. No.: WO2009/129457
PCT Pub. Date: Oct. 22, 2009

(65) Prior Publication Data
US 2011/0201916 A1    Aug. 18, 2011

Related U.S. Application Data

(60) Provisional application No. 61/045,782, filed on Apr. 17, 2008.

(51) Int. Cl.
*G01R 33/567* (2006.01)
*A61B 5/055* (2006.01)
(Continued)

(52) U.S. Cl.
CPC ............. *A61B 5/055* (2013.01); *A61B 5/05* (2013.01); *A61B 5/721* (2013.01);
(Continued)

(58) Field of Classification Search
None
See application file for complete search history.

(56) References Cited

U.S. PATENT DOCUMENTS 5,382,905 A * 1/1995 Miyata et al. ................ 324/319
5,446,548 A * 8/1995 Gerig ....................... A61B 6/08
250/462.1

(Continued)

FOREIGN PATENT DOCUMENTS

WO        00/72039 A    11/2000
WO      2007/136745 A   11/2007

OTHER PUBLICATIONS

International Search Report issued Jul. 7, 2009 in priority Application No. PCT/US2009/040948. 7 pages.
(Continued)

*Primary Examiner* — Katherine Fernandez
*Assistant Examiner* — Michael Kellogg
(74) *Attorney, Agent, or Firm* — Polsinelli PC; Ari M. Bai

(57) ABSTRACT

Provided are methods and systems for movement correction in an MRI environment. In one aspect, provided are systems and methods for movement correction, comprising receiving a first plurality of images from a first scan of a subject with a first camera, receiving magnetic resonance imaging (MRI) images obtained concurrently with the first scan, correlating the first plurality of images obtained from the first scan with the MRI images, resulting in motion correction data, and providing the motion correction data to an MRI system, wherein the MRI system adjusts scanning according to the motion correction data.

2 Claims, 8 Drawing Sheets

(51) Int. Cl.
*A61B 5/05* (2006.01)
*G01R 33/565* (2006.01)
*G06T 7/00* (2006.01)
*G06T 3/00* (2006.01)
*A61B 5/00* (2006.01)
*G01R 33/28* (2006.01)
*G01R 33/48* (2006.01)
*G01R 33/54* (2006.01)

(52) U.S. Cl.
CPC ...... *G01R 33/56509* (2013.01); *A61B 5/7207* (2013.01); *G01R 33/283* (2013.01); *G01R 33/4808* (2013.01); *G01R 33/543* (2013.01); *G06T 3/0068* (2013.01); *G06T 7/0024* (2013.01); *G06T 7/0026* (2013.01); *G06T 7/0028* (2013.01)

(56) References Cited

U.S. PATENT DOCUMENTS

| | | | | |
|---|---|---|---|---|
| 5,545,993 | A * | 8/1996 | Taguchi et al. | 324/309 |
| 5,947,900 | A * | 9/1999 | Derbyshire et al. | 600/410 |
| 6,798,925 | B1 * | 9/2004 | Wagman | G06T 7/0018 356/620 |
| 6,998,842 | B2 * | 2/2006 | Sinnema et al. | 324/318 |
| 8,781,553 | B2 * | 7/2014 | Kuhara | 600/413 |
| 8,971,992 | B2 * | 3/2015 | Kuhara | 600/413 |
| 2002/0118373 | A1 * | 8/2002 | Eviatar et al. | 356/614 |
| 2003/0135105 | A1 * | 7/2003 | Jack et al. | 600/410 |
| 2004/0017372 | A1 * | 1/2004 | Park | G06T 13/40 345/475 |
| 2004/0171927 | A1 * | 9/2004 | Lowen et al. | 600/410 |
| 2005/0033152 | A1 * | 2/2005 | Sinnema et al. | 600/410 |
| 2005/0054910 | A1 * | 3/2005 | Tremblay et al. | 600/411 |
| 2005/0265516 | A1 * | 12/2005 | Haider | 378/20 |
| 2005/0273000 | A1 * | 12/2005 | Dinehart et al. | 600/410 |
| 2005/0283068 | A1 * | 12/2005 | Zuccolotto et al. | 600/410 |
| 2007/0035303 | A1 * | 2/2007 | Gleich et al. | 324/322 |
| 2007/0108978 | A1 * | 5/2007 | MacFarlane | G01R 33/28 324/318 |
| 2008/0281186 | A1 * | 11/2008 | Kuhara | 600/413 |
| 2008/0287772 | A1 * | 11/2008 | Declerck et al. | 600/411 |
| 2011/0218424 | A1 * | 9/2011 | Kuhara | 600/413 |
| 2012/0245453 | A1 * | 9/2012 | Tryggestad et al. | 600/413 |
| 2013/0102879 | A1 * | 4/2013 | Maclaren et al. | 600/411 |
| 2013/0278263 | A1 * | 10/2013 | Huang et al. | 324/309 |
| 2015/0015255 | A1 * | 1/2015 | Krueger et al. | 324/309 |

OTHER PUBLICATIONS

Dold et al., "Prospective Head Motion Compensation for MRI by Updating the Gradients and Radio Frequency During Data Acquisition," Medical Image Computing and Computer-Assisted Intervention—MIC CAI 2005 Lecture Notes in Computer Science; LNCS, Springer, Berlin, DE, vol. 3749, Jan. 1, 2005, pp. 482-489.

Lerner et al., "Vision-based tracking system for head motion correction in fMRI images," Proceedings of the First International Conference on Computer Vision Theory and Applications: Setubal, Portugal, Feb. 25-28, 2006, INSTICC Press, pp. 213-220.

* cited by examiner

MOVEMENT CORRECTION IN MRI USING A CAMERA

CROSS REFERENCE TO RELATED PATENT APPLICATION

This is the national stage of International Application No. PCT/US2009/040948 filed Apr. 17, 2009, which claims the benefit of U.S. Provisional Application No. 61/045,782 filed Apr. 17, 2008, the contents of both of which are herein incorporated by reference in their entirety.

SUMMARY

In one aspect, provided are systems and methods for movement correction, comprising receiving a first plurality of images from a first scan of a subject with a first camera, receiving magnetic resonance imaging (MRI) images obtained concurrently with the first scan, correlating the first plurality of images obtained from the first scan with the MRI images, resulting in motion correction data, and providing the motion correction data to an MRI system, wherein the MRI system adjusts scanning according to the motion correction data.

In another aspect, provided are systems and methods for movement correction, comprising receiving a first plurality of images from a scan of a subject with a first camera, comparing the first plurality of images to a pre-classified plurality of images to determine similarities, wherein each pre-classified image has associated motion parameters, associating motion parameters from the pre-classified plurality of images with the similar images from the first plurality of images, updating motion correction data with the association, and providing the motion correction data to an MRI system, wherein the MRI system adjusts scanning according to the motion correction data.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
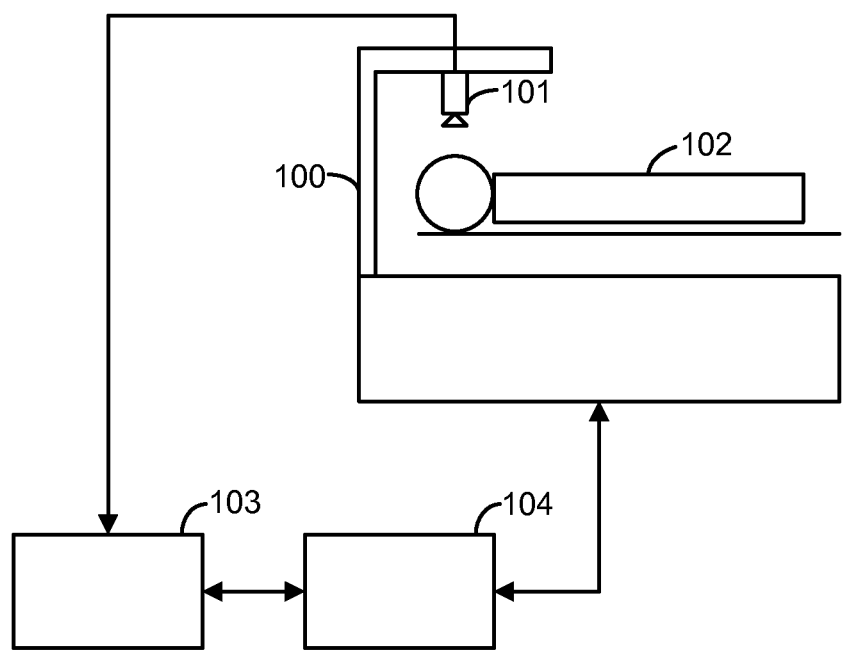
FIG. 1 is a block diagram describing an exemplary integration of a tracking system with MRI scanner hardware.

Before the present methods and systems are disclosed and described, it is to be understood that the methods and systems are not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment.

By a "subject" is meant an individual. The subject can be a vertebrate, for example, a mammal. Thus, the subject can be a human. The term does not denote a particular age or sex. The term subject includes small or laboratory animals as well as primates, including humans. A small animal includes, but is not limited to, a rodent such as a mouse or a rat. The term small animal is also used interchangeably with animal, laboratory animal, small laboratory animal, or subject, which includes mice, rats, cats, dogs, fish, rabbits, guinea pigs, rodents, etc. The term laboratory animal does not denote a particular age or sex. Thus, adult and newborn animals, whether male or female, are included.

The term "camera" as used herein is not limited in scope to any specific mechanism of operation for capture of an image. Both analog and digital camera systems may be used, cameras sensitive to any available range of electromagnetic radiation may be used (e.g., infrared), and any capture mechanism (e.g., charge-coupled devices, small area arrays, large area arrays, semiconductor photoresponse systems, electrophotoconductor response, lens focused systems, direct light impact systems, mirror directed systems, and the like) known in the art may be used.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

FIG. 1 is a block diagram describing an exemplary integration of a tracking system with MRI scanner 100 hardware. In the embodiment shown, one or more cameras 101 can be positioned to image a subject 102, or a portion of the subject 102. For example, the head of a subject 102. In an aspect, the one or more cameras 101 can be fixed above and in front of a head coil or on the magnet bore. As used herein, "fixed" means attached either permanently or temporarily. The position(s) of the one or more cameras 101 can be adjusted. By further example, the one or more cameras 101 can be located from 10-30 cm from the center of the object to be imaged.

Figure 2A:
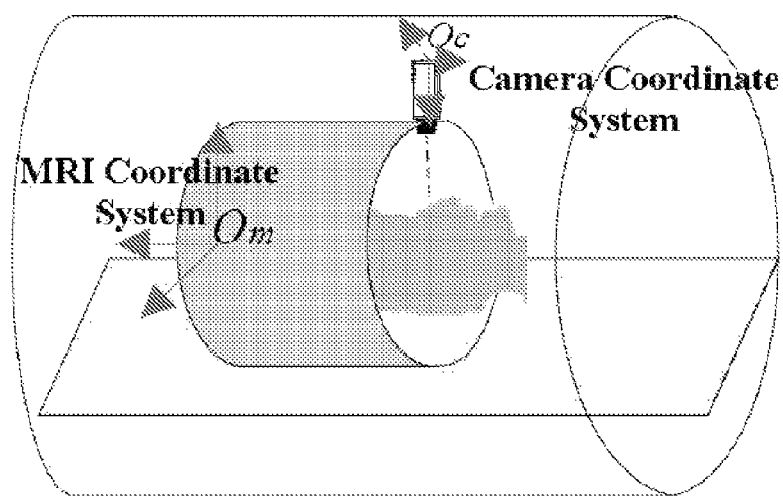
FIG. 2a is an illustration depicting exemplary camera position.
Figure 2B:
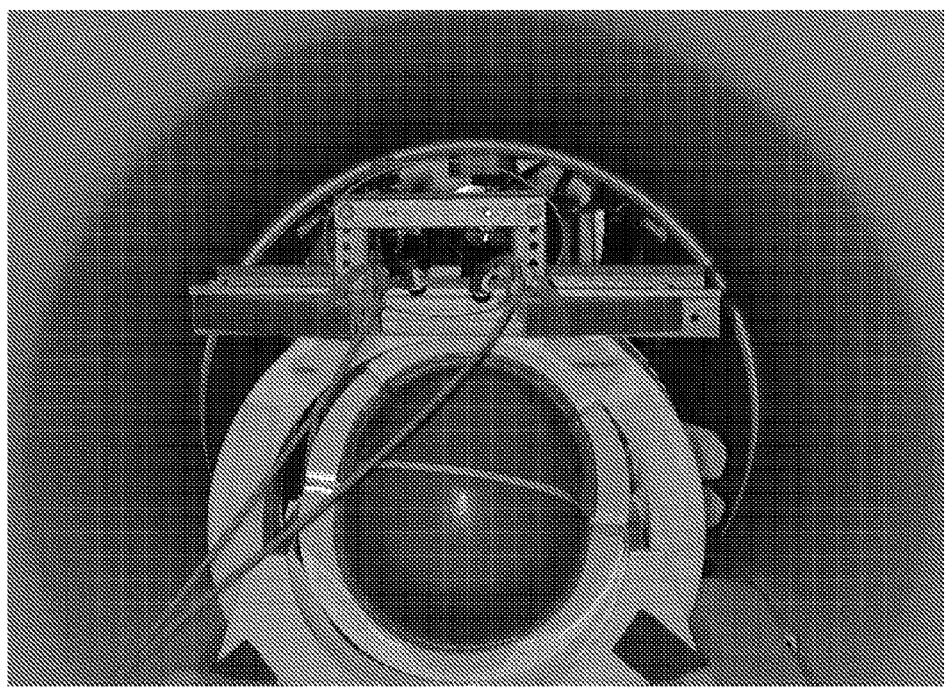
FIG. 2b is an image depicting exemplary camera position.

In one aspect, as shown in FIG. 2a and FIG. 2b, one or more MRI compatible infrared cameras (e.g. those available from MRC Systems GmbH, Germany) can be fixed on a holder above and in front of a head coil or on the magnet bore. The distance from the camera to the face of a subject in the implementation of FIG. 2b is about 10 cm. Surrounding the camera lens, six infrared emitting diodes can be used to illuminate the field of view. With this view, the spatial resolution can be about 100 μm, and sub-millimeter movements can be detected.

Returning to FIG. 1, the one or more cameras 101 can be coupled to a computing device 103. Computing device 103 can be any type of computing device, such as a server, a personal computer, and the like. Computing device 103 can receive images from the one or more cameras 101. Computing device 103 can be coupled to computing device 104. Computing device 104 can be an MRI control computer. In another aspect, the functions performed by computing devices 103 and 104 can be performed on a single computing device. Computing device 103 can receive MRI images from the computing device 104 or the MRI scanner 100. MRI images can be, for example, echo planar imaging (EPI) images, or any type of MRI image obtained by a rapid MRI technique. Thus, generating continuously updated motion correction data.

The system can be configured to trigger concurrent image acquisition by the one or more cameras 101 and the MRI scanner 100. The computing device 103 can receive concurrent images from the one or more cameras 101 and the MRI scanner 100. The computing device 103 can process the concurrent images to perform the methods described herein. The computing device 103 can provide movement correction data, for example, six degrees of freedom data including three rotations and three translations, to the computing device 104 and/or MRI scanner 100 in order to adjust MRI scanning parameters in real-time to account for subject movement.

In an aspect, communication among system components can be through a TCP/IP connection. Before each scan of the MRI scanner, the computing device 104 can read the current values of the continuously updated motion correction data to adjust, for example, the gradient rotation and offset phases and frequencies in the sequence to compensate for the changes in position. The gradient rotation can be updated based on the rotation parameters, the excitation frequency and the receiver frequency can be updated based on the translation in slice selection and frequency encoding direction, and the receiver phase can be updated based on the translation in phase encoding direction.

In one aspect, provided is a method utilizing a training scan to estimate head position and linking camera image measurement to the MRI scanner coordinate system. In one aspect, during the training scan, a subject can move his head in the directions that are least restrained, including rotations in the axial, coronal and sagittal planes. A series of EPI images (with, for example, parameters: 64×48 voxels over 24×18 $cm^2$, 18 2 mm slices with 2 mm gap, TE 20 ms, TR 1 s) and camera images can be acquired simultaneously. From the camera images, one or more image features can be extracted to serve as indicators of head position. For example, local features including interest points, localized regions, etc., and global features including shape, texture, etc. In an aspect, the system can utilize facial recognition software to extract landmarks from a subjects face. For example, the position, size, and/or shape of the eyes, nose, cheekbones, jaw, etc. These extracted landmarks can serve as feature points to determine motion. From the EPI images, motion parameters in the MRI coordinate system (for example, three rotations and three translations) between each volume can be determined (for example, with 3D registration). Since the camera images were acquired simultaneously with the EPI images, each camera image can correspond to one or more motion parameters. In a non-training scan, newly captured camera images can be compared with the training camera images to find the most similar images. For example, by extracting image feature points from the newly acquired images and calculating the distance between those feature points to the corresponding feature points extracted from the training images to find the minimum distance. The summation of distance between feature points from two images can be used to judge the similarity.

In one aspect, an average of the corresponding motion parameters of the training images can serve as the estimation of the current head position. Several most similar images to the newly captured images can be determined from the training images, and the average of their motion parameters can provide a more accurate estimation of the current motion.

Figure 3:
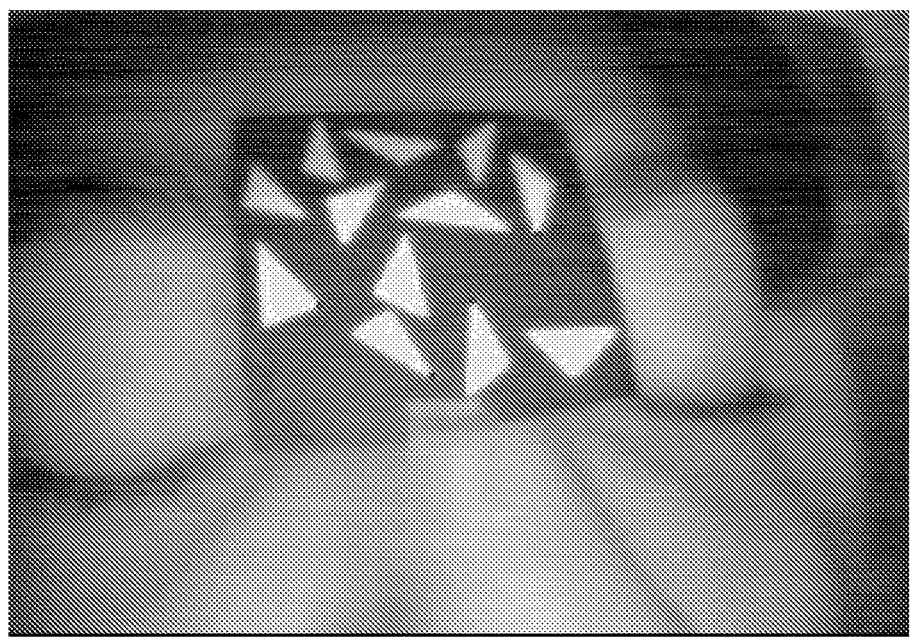
FIG. 3 is an image depicting patterned paper on a subject's face.

The methods and systems provided can estimate head motion from facial features. However, determining similarity between images can utilize non-facial features. As shown in FIG. 3, by way of example and not limitation, a dark 4×3 $cm^2$ paper with white triangles can be fixed on the forehead of the subject. The corners of the triangles can be extracted and used as feature points during image analysis. Any similar image can be used, regardless of shape, size or contrast.

In an aspect utilizing a plurality of cameras, the MRI scanner and the plurality of cameras can be triggered to acquire images concurrently. The training step for each camera can be the same as in the single camera case (as shown in FIG. 4), but the estimation of current head position can be the average or weighted average of motion parameters from the plurality of cameras.

Figure 4:
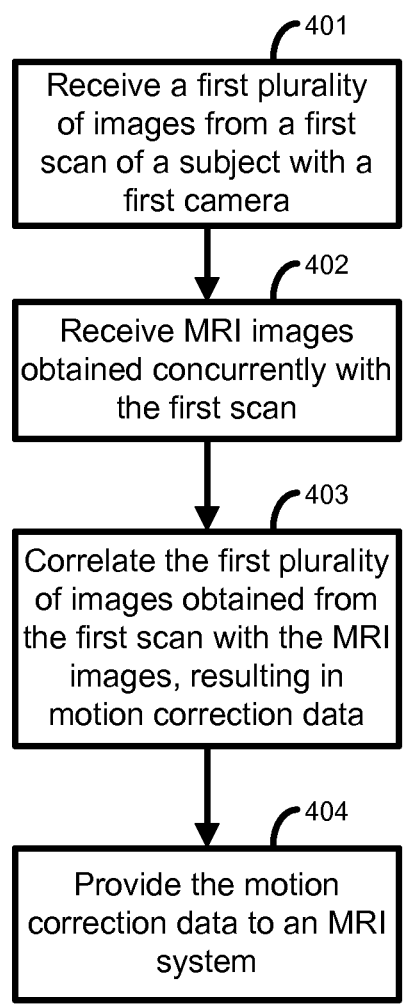
FIG. 4 is an exemplary method.

In one aspect, illustrated in FIG. 4, provided are methods for movement correction, comprising receiving a first plurality of images from a first scan of a subject with a first camera at 401, receiving MRI images obtained concurrently with the first scan at 402, correlating the first plurality of images obtained from the first scan with the MRI images, resulting in motion correction data at 403, and providing the motion correction data to an MRI system at 404, wherein the MRI system adjusts scanning according to the motion correction data. The steps of the method can be performed wholly or in part by one or more computing devices. In an aspect, one computing device can perform all the steps. In another aspect, more than one computing device can perform all the steps.

Correlating the first plurality of images obtained from the first scan with the MRI images, resulting in motion correction data can further comprise extracting an image feature from the first plurality of images, deriving motion parameters from the MRI images, and associating the image feature from each image with the motion parameters from each concurrent MRI image. The correlation step involves transforming image data into motion correction data utilized to adjust the scanning parameters utilized by an MRI scanner.

In an aspect, the methods can utilize more than one camera. Receiving a first plurality of images from a first scan of a subject with a first camera can further comprise receiving a second plurality of images from the first scan of the subject with a second camera. Correlating the first plurality of images obtained from the first scan with the MRI images, resulting in motion correction data, can further comprise correlating the second plurality of images obtained from the first scan with the MRI images, resulting in motion correction data.

The methods can further comprise receiving a third plurality of images from a second scan of the subject with the first camera, extracting an image feature from the third plurality of images, comparing the image feature from the third plurality of images with the image feature from the first plurality of images to determine similarities, associating motion parameters from the first plurality of images with the similar images from the third plurality of images, and updating the motion correction data with the association. The methods can further comprise adjusting an MRI parameter based on the motion correction data in real-time.

Figure 5:
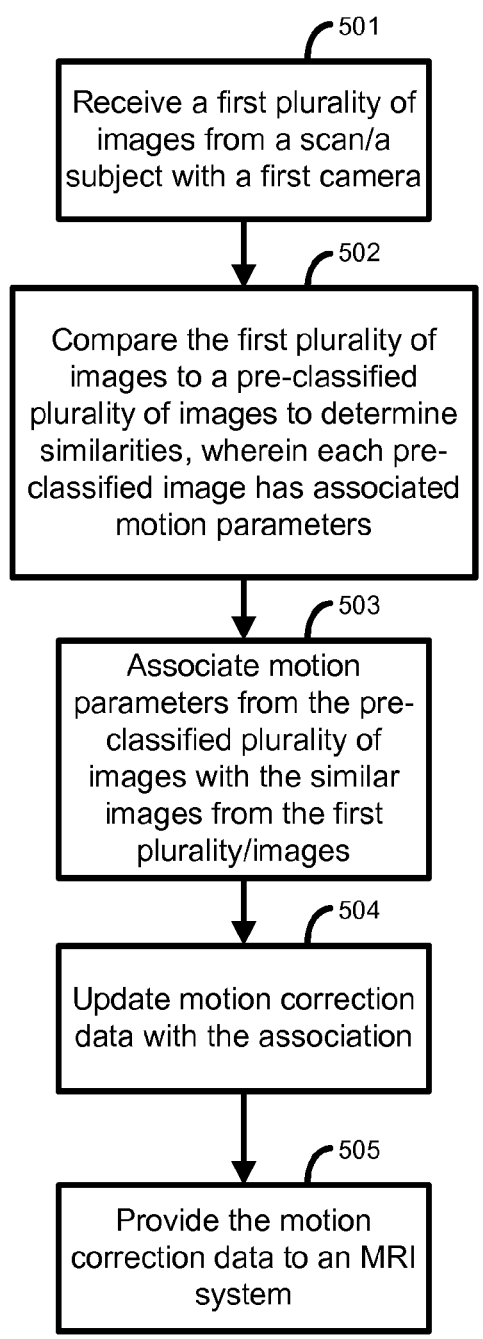
FIG. 5 is another exemplary method.

In another aspect, illustrated in FIG. 5, provided are methods for movement correction, comprising receiving a first plurality of images from a scan of a subject with a first camera at 501, comparing the first plurality of images to a pre-classified plurality of images to determine similarities, wherein each pre-classified image has associated motion parameters at 502, associating motion parameters from the pre-classified plurality of images with the similar images from the first plurality of images at 503, updating motion correction data with the association at 504, and providing the motion correction data to an MRI system at 505, wherein the MRI system adjusts scanning according to the motion correction data. The methods can further comprise adjusting an MRI parameter based on the motion correction data. The MRI system can utilize the updated motion correction data to account for motion during real-time scanning. The pre-classified plurality of images can be generated, for example, according to the methods described in FIG. 4. The pre-classified plurality of images and the associated motion parameters can comprise a translation table wherein an image feature of a newly acquired image can be found in the table and associated motion parameters determined. Image data that is obtained from the scans is thus transformed into motion correction data utilized to adjust the scanning parameters utilized by an MRI scanner. The steps of the method can be performed wholly or in part by one or more computing devices. In an aspect, one computing device can perform all the steps. In another aspect, more than one computing device can perform all the steps.

In an aspect, the methods can utilize more than one camera. Receiving a first plurality of images from a scan of a subject with a first camera can further comprise receiving a second plurality of images from a scan of the subject with a second camera. Comparing the first plurality of images to a pre-classified plurality of images to determine similarities, wherein each pre-classified image has associated motion parameters can further comprise comparing the second plurality of images to the pre-classified plurality of images to determine similarities. Associating motion parameters from the pre-classified plurality of images with the similar images from the first plurality of images can further comprise associating motion parameters from the pre-classified plurality of images with the similar images from the second plurality of images.

In an aspect, provided is a system for movement correction, comprising a first camera, configured to image a subject, a magnetic resonance imaging (MRI) device, configured to obtain MRI images concurrently with the first camera, and a computing device, coupled to the first camera and the MRI device, configured for receiving a first plurality of images from a first scan of a subject with the first camera, receiving MRI images obtained concurrently with the first scan, correlating the first plurality of images obtained from the first scan with the MRI images, resulting in motion correction data, and providing the motion correction data to the MRI device, wherein the MRI device adjusts scanning according to the motion correction data. In an aspect, one computing device can perform the steps described and in another aspect, more than one computing device can perform the steps described.

Correlating the first plurality of images obtained from the first scan with the MRI images, resulting in motion correction data can comprise extracting an image feature from the first plurality of images, deriving motion parameters from the MRI images, and associating the image feature from each image with the motion parameters from each concurrent MRI image.

Receiving a first plurality of images from a first scan of a subject with a first camera, can further comprise receiving a second plurality of images from the first scan of the subject with a second camera.

Correlating the first plurality of images obtained from the first scan with the MRI images, resulting in motion correction data, can further comprise correlating the second plurality of images obtained from the first scan with the MRI images, resulting in motion correction data.

The computing device can be further configured for receiving a third plurality of images from a second scan of the subject with the first camera, extracting an image feature from the third plurality of images, comparing the image feature from the third plurality of images with the image feature from the first plurality of images to determine similarities, associating motion parameters from the first plurality of images with the similar images from the third plurality of images, and updating the motion correction data with the association.

The computing device can be further configured for adjusting an MRI parameter based on the motion correction data in real-time.

In an aspect, provided is a system for movement correction, comprising a first camera, configured to image a subject, a magnetic resonance imaging (MRI) device, configured to obtain MRI images concurrently with the first camera, and a computing device, coupled to the first camera and the MRI device, configured for receiving a first plurality of images from a scan of a subject with the first camera comparing the first plurality of images to a pre-classified plurality of images to determine similarities, wherein each pre-classified image has associated motion parameters associating motion parameters from the pre-classified plurality of images with the similar images from the first plurality of images, updating motion correction data with the association, and providing the motion correction data to the MRI device, wherein the MRI device adjusts scanning according to the motion correction data.

Receiving a first plurality of images from a scan of a subject with a first camera can further comprise receiving a second plurality of images from a scan of the subject with a second camera.

Comparing the first plurality of images to a pre-classified plurality of images to determine similarities, wherein each pre-classified image has associated motion parameters can further comprise comparing the second plurality of images to the pre-classified plurality of images to determine similarities.

Associating motion parameters from the pre-classified plurality of images with the similar images from the first plurality of images can further comprise associating motion parameters from the pre-classified plurality of images with the similar images from the second plurality of images.

The computing device can be further configured for adjusting an MRI parameter based on the motion correction data in real-time.

In an aspect, provided is an apparatus for or movement correction, comprising a first camera, configured to image a subject, a memory, configured for storing image data, a processor, coupled to the first camera and the memory, configured for receiving a first plurality of images from a first scan of a subject with the first camera, receiving MRI images from an MRI system obtained concurrently with the first scan, correlating the first plurality of images obtained from the first scan with the MRI images, resulting in motion correction data, and providing the motion correction data to the MRI system, wherein the MRI system adjusts scanning according to the motion correction data.

Correlating the first plurality of images obtained from the first scan with the MRI images, resulting in motion correction data can comprise extracting an image feature from the first plurality of images, deriving motion parameters from the MRI images, and associating the image feature from each image with the motion parameters from each concurrent MRI image.

The apparatus can further comprise a second camera and wherein receiving a first plurality of images from a first scan of a subject with a first camera, further comprises receiving a second plurality of images from the first scan of the subject with the second camera.

Correlating the first plurality of images obtained from the first scan with the MRI images, resulting in motion correction data, can further comprise correlating the second plurality of images obtained from the first scan with the MRI images, resulting in motion correction data.

The processor can be further configured for receiving a third plurality of images from a second scan of the subject with the first camera, extracting an image feature from the third plurality of images, comparing the image feature from the third plurality of images with the image feature from the first plurality of images to determine similarities, associating motion parameters from the first plurality of images with the similar images from the third plurality of images, and updating the motion correction data with the association. The processor can be further configured for adjusting an MRI parameter based on the motion correction data in real-time.

In an aspect, provided is an apparatus for or movement correction, comprising a first camera, configured to image a subject, a memory, configured for storing image data, a processor, coupled to the first camera and the memory, configured for receiving a first plurality of images from a scan of a subject with the first camera, comparing the first plurality of images to a pre-classified plurality of images to determine similarities, wherein each pre-classified image has associated motion parameters, associating motion parameters from the pre-classified plurality of images with the similar images from the first plurality of images, updating motion correction data with the association, and providing the motion correction data to an MRI system, wherein the MRI system adjusts scanning according to the motion correction data.

The apparatus can further comprise a second camera and wherein receiving a first plurality of images from a scan of a subject with a first camera further comprises receiving a second plurality of images from a scan of the subject with the second camera.

Comparing the first plurality of images to a pre-classified plurality of images to determine similarities, wherein each pre-classified image has associated motion parameters can further comprise comparing the second plurality of images to the pre-classified plurality of images to determine similarities.

Associating motion parameters from the pre-classified plurality of images with the similar images from the first plurality of images can further comprise associating motion parameters from the pre-classified plurality of images with the similar images from the second plurality of images. The processor can be further configured for adjusting an MRI parameter based on the motion correction data in real-time.

Figure 6:
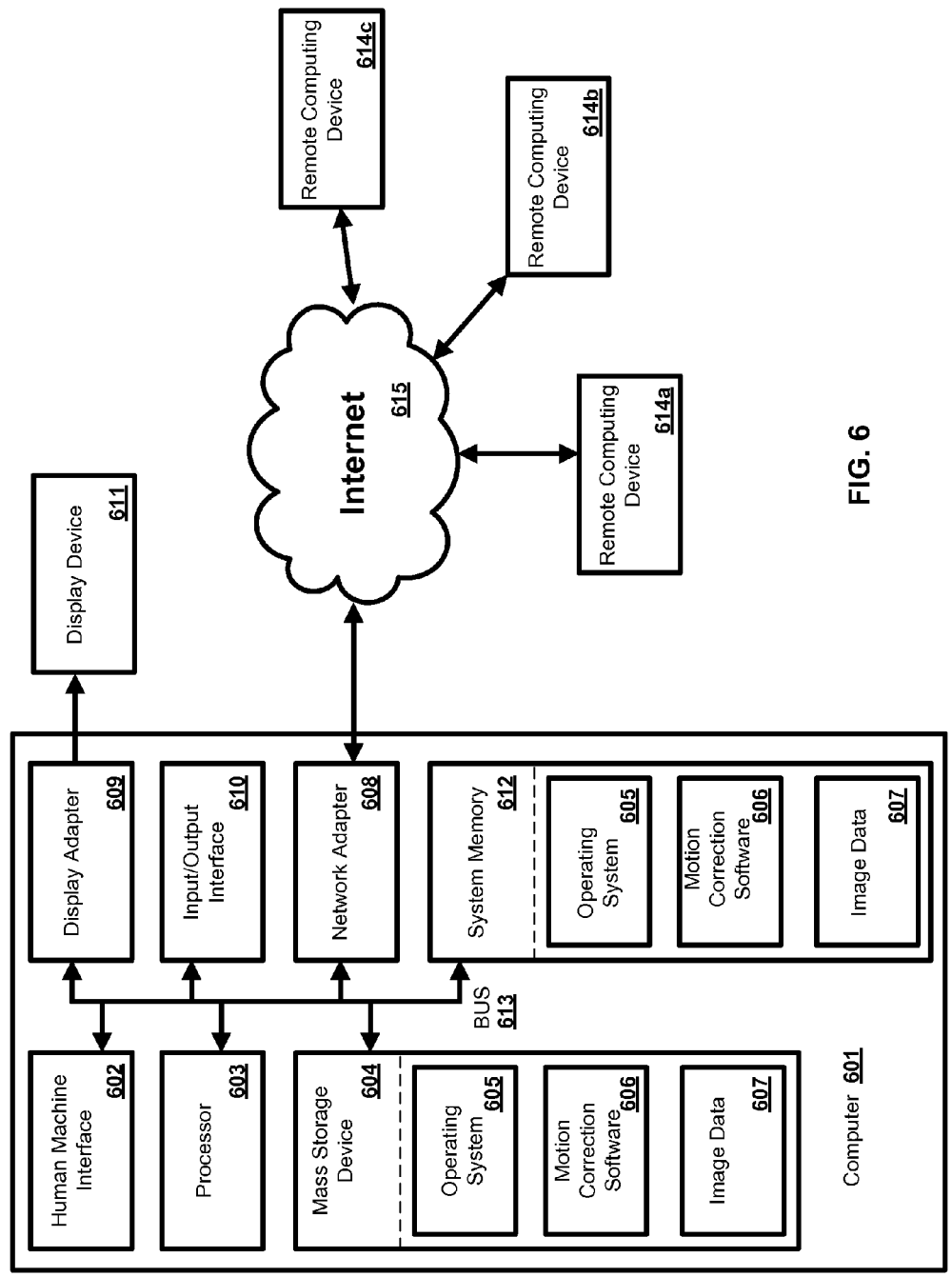
FIG. 6 is an exemplary computing device capable of performing the disclosed methods.

The methods disclosed can be performed on one or more computing devices. One skilled in the art will appreciate that what is provided is a functional description and that the respective functions can be performed by software, hardware, or a combination of software and hardware. FIG. 6 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed system and method can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed method can also be practiced in grid-based and distributed computing environments where tasks are performed by remote processing devices that are linked through a communications network. In a distributed computing environment, program modules can be located in both local and remote computer storage media including memory storage devices. In an embodiment, one or more of the methods disclosed can be embodied on an electromagnetic signal.

Further, one skilled in the art will appreciate that the system and method disclosed herein can be implemented via a general-purpose computing device in the form of a computer 601. The components of the computer 601 can comprise, but are not limited to, one or more processors or processing units 603, a system memory 612, and a system bus 613 that couples various system components including the processor 603 to the system memory 612. In the case of multiple processing units 603, the system can utilize parallel computing.

The system bus 613 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 613, and all buses specified in this description can also be implemented over a wired or wireless network connection and each of the subsystems, including the processor 603, a mass storage device 604, an operating system 605, motion correction software 606, image data 607, a network adapter 608, system memory 612, an Input/Output Interface 610, a display adapter 609, a display device 611, and a human machine interface 602, can be contained within one or more remote computing devices 614a,b,c at physically separate locations, connected through buses of this form, in effect implementing a fully distributed system.

The computer 601 typically comprises a variety of computer readable media. Exemplary readable media can be any available media that is accessible by the computer 601 and comprises, for example and not meant to be limiting, both volatile and non-volatile media, removable and non-removable media. The system memory 612 comprises computer readable media in the form of volatile memory, such as random access memory (RAM), and/or non-volatile memory, such as read only memory (ROM). The system memory 612 typically contains data such as image data 607 and/or program modules such as operating system 605 and motion correction software 606 that are immediately accessible to and/or are presently operated on by the processing unit 603.

In another aspect, the computer 601 can also comprise other removable/non-removable, volatile/non-volatile computer storage media. By way of example, FIG. 6 illustrates a mass storage device 604 which can provide non-volatile storage of computer code, computer readable instructions, data structures, program modules, and other data for the computer 601. For example and not meant to be limiting, a mass storage device 604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 604, including by way of example, an operating system 605 and motion correction software 606. Each of the operating system 605 and motion correction software 606 (or some combination thereof) can comprise elements of the programming and the motion correction software 606. Image data 607 can also be stored on the mass storage device 604. Image data 607 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems. Image data 607 can comprise, for example, images acquired from a camera, EPI images, image correlation data, motion correction data, and the like.

In another aspect, the user can enter commands and information into the computer 601 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 603 via a human machine interface 602 that is coupled to the system bus 613, but can be connected by other interface and bus structures, such as a parallel port, game port, an IEEE 1394 Port (also known as a Firewire port), a serial port, or a universal serial bus (USB).

In yet another aspect, a display device 611 can also be connected to the system bus 613 via an interface, such as a display adapter 609. It is contemplated that the computer 601 can have more than one display adapter 609 and the computer 601 can have more than one display device 611. For example, a display device can be a monitor, an LCD (Liquid Crystal Display), or a projector. In addition to the display device 611, other output peripheral devices can comprise components such as speakers (not shown) and a printer (not shown) which can be connected to the computer 601 via Input/Output Interface 610. Any step and/or result of the methods can be output in any form to an output device. Such output can be any form of visual representation, including, but not limited to, textual, graphical, animation, audio, tactile, and the like.

The computer 601 can operate in a networked environment using logical connections to one or more remote computing devices 614a,b,c. By way of example, a remote computing device can be a personal computer, portable computer, a server, a router, a network computer, a peer device or other common network node, and so on. Logical connections between the computer 601 and a remote computing device 614a,b,c can be made via a local area network (LAN) and a general wide area network (WAN). Such network connections can be through a network adapter 608. A network adapter 608 can be implemented in both wired and wireless environments. Such networking environments are conventional and commonplace in offices, enterprise-wide computer networks, intranets, and the Internet 615.

For purposes of illustration, application programs and other executable program components such as the operating system 605 are illustrated herein as discrete blocks, although it is recognized that such programs and components reside at various times in different storage components of the computing device 601, and are executed by the data processor(s) of the computer. An implementation of motion correction software 606 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

In an example, experiments were performed using a GE 7T scanner. A stability test was carried out where the system tracked a stationary object for several minutes. The output of the tracking system is summarized in Table 1, showing only very small position fluctuations.

TABLE 1

Stability of the tracking system.

| | X (µm) | Y (µm) | Z (µm) | RX ($10^{-3}$°) | RY ($10^{-3}$°) | RZ ($10^{-3}$°) |
|---|---|---|---|---|---|---|
| Mean | 0.8 | −11.3 | 4.7 | −3.3 | −0.7 | 0.5 |
| Std | 32.1 | 83.4 | 11.7 | 24.2 | 9.2 | 5.4 |

Figures 7A, 7B, 7C:
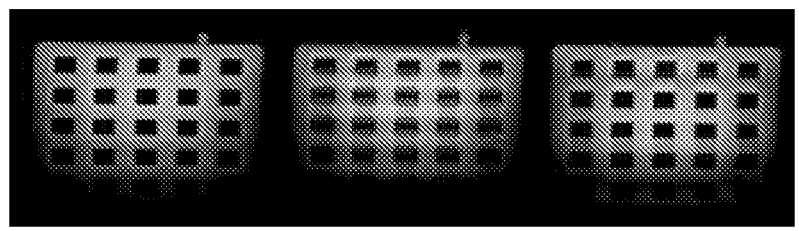
FIG. 7a is an image depicting a calibration phantom image with no motion.
FIG. 7b is an image depicting the calibration phantom image with motion and to motion correction.
FIG. 7c is an image depicting the calibration phantom image with motion and with motion correction.

Motion correction results are shown in FIG. 7a, FIG. 7b, and FIG. 7c. A multi-shot gradient echo sequence was used, with TE 4.2 ms, TR 1.5 s, flip angle 20. FIG. 7a shows the calibration phantom image with no motion. FIG. 7b and FIG. 7c were acquired with motion during the scan, where FIG. 7b is uncorrected and in FIG. 7c motion is corrected. The motion was about a 7 mm step in the vertical direction in the image, approximately performed at the moment the center of k-space was acquired.

In another example, to estimate the accuracy of the methods provided, five minutes of data were acquired, consisting of 300 EPI volumes and 300 camera images. The data were divided into a training set and a testing set. All the EPI images in the training set were registered to a reference (any one volume in the training set can be used as a reference) to obtain motion parameters. For every camera image in the testing set, the most similar images in the training set were determined based on the distance of feature points. The average motion parameters of these training images served as a motion estimate for that test image, whereas the true motion was derived by registration of the test EPI image to the reference.

Figure 8:
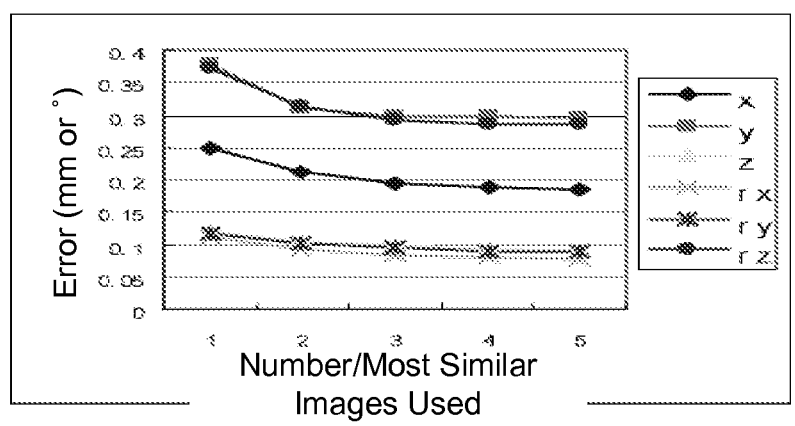
FIG. 8 illustrates resulting average errors as function of the number of images from a training set used to estimate motion.

A k-fold cross-validation method was used to evaluate the estimation error, where k was chosen equal to ten. For each trial, thirty images were selected for the testing set, while the remaining 270 formed the training set. This was repeated ten times for different test sets. Then, the average error (difference between camera derived position and EPI registration parameters) across the ten trials was determined. The result of cross-validation was a random number that depended on the division of samples into subsets. So, in order to obtain more accurate error estimation, the 10-fold cross-validation was repeated 100 times using different selections of the subsets. The mean of the associated 100 errors were then calculated. FIG. 8 shows the resulting average errors as function of the number of images from the training set used to estimate the motion. The largest errors were from translation in the y direction and rotation about the z axis. This was because the camera was approximately facing the MRI system's y axis, resulting in a lower sensitivity in y compared to x and z.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for motion correction in a magnetic resonance imaging (MRI) system, comprising:
    generating a training scan, comprising the steps of:

receiving a plurality of training camera images from a training scan of a subject or a portion thereof obtained by a camera;

receiving a plurality of training MRI images of the subject or portion thereof obtained by an MRI device, the plurality of training MRI images being obtained concurrently with the plurality of training camera images, wherein each one of the plurality of training camera images corresponds to a respective one of the plurality of training MRI images as a function of time;

using a processor to perform the steps of:
   extracting one or more training image features from each of the plurality of training camera images;
   using an image registration algorithm to derive motion parameters from the plurality of training MRI images, the motion parameters being parameters in a three-dimensional MRI coordinate system; and
   generating a translation table in which each entry in the translation table assigns to each of the plurality of training camera images the motion parameters derived from each corresponding concurrent training MRI image of the plurality of training MRI images;

generating a testing scan using the processor to perform the steps of:
   receiving a plurality of testing camera images of the subject or portion thereof obtained with the camera;
   extracting one or more testing image features of the subject or a portion thereof from the testing camera images;
   comparing the testing camera images with the training camera images to find the most similar images between the training camera images and the testing camera images, wherein the position of each testing image feature on the subject or portion thereof corresponds to a training image feature, and calculating the distance between the one or more testing image features and the corresponding one or more training image features to find the minimum distance between the one or more testing image features and the one or more training image features, wherein the one or more testing image features and the one or more training image features are locations in a physical space, wherein the summation of distance between the one or more training and testing image features in the physical space indicates the similarity thereof; and
   receiving a plurality of testing MRI images obtained by the MRI device, the plurality of testing MRI images being obtained concurrently with the plurality of testing camera images, wherein each testing camera image corresponds to a testing MRI image as a function of time; and applying a motion correction to the plurality of testing MRI images by providing the data from translation table to the MRI system, wherein the MRI device adjusts MRI scanning parameters comprising gradient rotation and offset phases and frequencies in the MRI scanner sequence in real-time according to motion parameters in the translation table that are assigned to the training camera image that is most similar to the testing camera image to account for motion of the subject or portion thereof during the testing scan.

2. The method of claim 1, wherein the MRI device adjusts MRI scanning parameters comprising gradient rotation and offset phases and frequencies in an MRI scanner sequence in real-time according to the motion parameters in the translation table that are assigned to the training camera image that is most similar to the testing camera image to account for motion of the subject or portion thereof during the testing scan.

* * * * *